United States Patent
Better et al.

(10) Patent No.: US 7,247,454 B2
(45) Date of Patent: Jul. 24, 2007

(54) METHODS FOR RECOMBINANT PEPTIDE PRODUCTION

(75) Inventors: Marc D. Better, Los Angeles, CA (US); Patrick D. Gavit, Covina, CA (US)

(73) Assignee: XOMA Technology Ltd., Berkeley, CA (US)

( * ) Notice: Subject to any disclaimer, the term of this patent is extended or adjusted under 35 U.S.C. 154(b) by 286 days.

(21) Appl. No.: 10/324,182

(22) Filed: Dec. 20, 2002

(65) Prior Publication Data

US 2003/0194782 A1    Oct. 16, 2003

Related U.S. Application Data

(63) Continuation of application No. 09/760,397, filed on Jan. 12, 2001, now Pat. No. 6,500,648, which is a continuation of application No. 09/271,970, filed on Mar. 18, 1999, now Pat. No. 6,242,219.

(51) Int. Cl.
*C12P 21/04* (2006.01)
*C07K 1/00* (2006.01)
*B01N 33/53* (2006.01)

(52) U.S. Cl. .............. 435/69.7; 435/7.1; 435/18; 435/69.1; 530/300; 530/350; 530/351; 530/412

(58) Field of Classification Search .............. 435/69.7; 530/351, 412
See application file for complete search history.

(56) References Cited

U.S. PATENT DOCUMENTS

| | | | | |
|---|---|---|---|---|
| 5,130,415 | A | * 7/1992 | Tecce et al. | 530/324 |
| 5,851,802 | A | * 12/1998 | Better | 435/69.7 |
| 6,242,219 | B1 | * 6/2001 | Better et al. | 435/69.7 |
| 6,500,648 | B1 | * 12/2002 | Better et al. | 435/69.7 |

OTHER PUBLICATIONS

Szoka et al (DNA (1986) 5(1):11-20).*
Powell (ACS Symp. Ser. (1994) 567:100-17 Abstract Only.*
Nicosia et al (Infection and Immunity (1987) 55(4):963-967).*

* cited by examiner

*Primary Examiner*—Jeffrey Fredman
(74) *Attorney, Agent, or Firm*—Anne S. Dollard; John M. Polo; Janet M. McNicholas

(57) ABSTRACT

The present invention provides improved methods for the production of recombinant peptides from bacterial cells.

21 Claims, No Drawings

SEQUENCE LISTING

```
<160> NUMBER OF SEQ ID NOS: 16

<210> SEQ ID NO 1
<211> LENGTH: 557
<212> TYPE: DNA
<213> ORGANISM: Human
<220> FEATURE:
<221> NAME/KEY: CDS
<222> LOCATION: (66)..(548)
<220> FEATURE:
<221> NAME/KEY: misc_feature
<222> LOCATION: (1)..(65)
<223> OTHER INFORMATION: /label= EcoRI /note="residues 1-65 comprise
      EcoRI site to beginning of pel B."
<220> FEATURE:
<221> NAME/KEY: misc_feature
<222> LOCATION: (1)..(22)
<223> OTHER INFORMATION: /label=pel B /note="pel B is the leader
      sequence from the pectate lyase gene of Erwiniacarotovora."
<220> FEATURE:
<221> NAME/KEY: misc_feature
<222> LOCATION: (23)..(161)
<223> OTHER INFORMATION: /label="Bone D" /note="Bone D is the subunit of
      human osteogenic protein (see, U.S. Patent No.
      5,284,756 e.g., Fig. 6, Example 9, Seq ID Nos: 1
      and 2."
<220> FEATURE:
<221> NAME/KEY: misc_feature
```

```
<222> LOCATION: (549)..(557)
<223> OTHER INFORMATION: /label=XHoI /note="residues 549-557 comprise
      stop codon and XhoI site."

<400> SEQUENCE: 1
gaattcctgc aggtctatgg aacgataaat gcccatgaaa attctatttc aaggagacag      60 tcata atg aaa tac cta ttg cct acg gca gcc gct gga ttg tta tta ctc     110
      Met Lys Tyr Leu Leu Pro Thr Ala Ala Ala Gly Leu Leu Leu Leu
       1               5                  10                  15 gct gcc caa cca gcg atg gcg tcc acg ggg agc aaa cag cgc agc cag       158
Ala Ala Gln Pro Ala Met Ala Ser Thr Gly Ser Lys Gln Arg Ser Gln
                20                  25                  30 aac cgc tcc aag acg ccc aag aac cag gaa gcc ctg cgg atg gcc aac       206
Asn Arg Ser Lys Thr Pro Lys Asn Gln Glu Ala Leu Arg Met Ala Asn
            35                  40                  45 gtg gca gag aac agc agc agc gac cag agg cag gcc tgt aag aag cac       254
Val Ala Glu Asn Ser Ser Ser Asp Gln Arg Gln Ala Cys Lys Lys His
        50                  55                  60 gag ctg tat gtc agc ttc cga gac ctg ggc tgg cag gac tgg atc atc       302
Glu Leu Tyr Val Ser Phe Arg Asp Leu Gly Trp Gln Asp Trp Ile Ile
    65                  70                  75 gcg cct gaa ggc tac gcc gcc tac tac tgt gag ggg gag tgt gcc ttc       350
Ala Pro Glu Gly Tyr Ala Ala Tyr Tyr Cys Glu Gly Glu Cys Ala Phe
 80                  85                  90                  95 cct ctg aac tcc tac atg aac gcc acc aac cac gcc atc gtg cag acg       398
Pro Leu Asn Ser Tyr Met Asn Ala Thr Asn His Ala Ile Val Gln Thr
                100                 105                 110 ctg gtc cac ttc atc aac ccg gaa acg gtg ccc aag ccc tgc tgt gcg       446
Leu Val His Phe Ile Asn Pro Glu Thr Val Pro Lys Pro Cys Cys Ala
            115                 120                 125 ccc acg cag ctc aat gcc atc tcc gtc ctc tac ttc gat gac agc tcc       494
Pro Thr Gln Leu Asn Ala Ile Ser Val Leu Tyr Phe Asp Asp Ser Ser
        130                 135                 140 aac gtc atc ctg aag aaa tac aga aac atg gtg gtc cgg gcc tgt ggc       542
Asn Val Ile Leu Lys Lys Tyr Arg Asn Met Val Val Arg Ala Cys Gly
    145                 150                 155 tgc cac tagctcgag                                                      557
Cys His
160

<210> SEQ ID NO 2
<211> LENGTH: 161
<212> TYPE: PRT
<213> ORGANISM: Human

<400> SEQUENCE: 2

Met Lys Tyr Leu Leu Pro Thr Ala Ala Ala Gly Leu Leu Leu Leu Ala
 1               5                  10                  15

Ala Gln Pro Ala Met Ala Ser Thr Gly Ser Lys Gln Arg Ser Gln Asn
                20                  25                  30

Arg Ser Lys Thr Pro Lys Asn Gln Glu Ala Leu Arg Met Ala Asn Val
            35                  40                  45

Ala Glu Asn Ser Ser Ser Asp Gln Arg Gln Ala Cys Lys Lys His Glu
        50                  55                  60

Leu Tyr Val Ser Phe Arg Asp Leu Gly Trp Gln Asp Trp Ile Ile Ala
    65                  70                  75                  80

Pro Glu Gly Tyr Ala Ala Tyr Tyr Cys Glu Gly Glu Cys Ala Phe Pro
                85                  90                  95

Leu Asn Ser Tyr Met Asn Ala Thr Asn His Ala Ile Val Gln Thr Leu
```

-continued

```
                  100                 105                 110
Val His Phe Ile Asn Pro Glu Thr Val Pro Lys Pro Cys Cys Ala Pro
        115                 120                 125

Thr Gln Leu Asn Ala Ile Ser Val Leu Tyr Phe Asp Asp Ser Ser Asn
    130                 135                 140

Val Ile Leu Lys Lys Tyr Arg Asn Met Val Arg Ala Cys Gly Cys
145                 150                 155                 160
His

<210> SEQ ID NO 3
<211> LENGTH: 12
<212> TYPE: PRT
<213> ORGANISM: Human

<400> SEQUENCE: 3

Lys Val Gly Trp Leu Ile Gln Leu Phe His Lys Lys
  1               5                  10

<210> SEQ ID NO 4
<211> LENGTH: 51
<212> TYPE: DNA
<213> ORGANISM: Human

<400> SEQUENCE: 4
gatccaccga aagtgggttg gctgatccag ctgttccaca aaaagtaaag c            51

<210> SEQ ID NO 5
<211> LENGTH: 51
<212> TYPE: DNA
<213> ORGANISM: Human

<400> SEQUENCE: 5
tcgagcttta cttttttgtgg aacagctgga tcagccaacc cactttcggt g           51

<210> SEQ ID NO 6
<211> LENGTH: 15
<212> TYPE: PRT
<213> ORGANISM: Human

<400> SEQUENCE: 6

Asp Pro Pro Lys Val Gly Trp Leu Ile Gln Leu Phe His Lys Lys
  1               5                  10                  15

<210> SEQ ID NO 7
<211> LENGTH: 610
<212> TYPE: DNA
<213> ORGANISM: Human
<220> FEATURE:
<221> NAME/KEY: CDS
<222> LOCATION: (66)..(599)
<220> FEATURE:
<221> NAME/KEY: misc_feature
<222> LOCATION: (1)..(65)
<223> OTHER INFORMATION: /label=EcoRI /note="residues 1-65 comprise
      EcoRI site to beginning of pel B."
<220> FEATURE:
<221> NAME/KEY: misc_feature
<222> LOCATION: (1)..(22)
<223> OTHER INFORMATION: /label=pel B /note="pel B is the leader
      sequence from the pectate lyase gene of Erwiniacaratovora."
<220> FEATURE:
<221> NAME/KEY: misc_feature
<222> LOCATION: (23)..(161)
<223> OTHER INFORMATION: /label="Bone D" /note="Bone D is the subunit of
      human osteogenic protein (see, U.S. Patent No.
      5,284,756 e.g., Fig. 6, Example 9, Seq ID Nos: 1
      and 2."
```

```
<220> FEATURE:
<221> NAME/KEY: misc_feature
<222> LOCATION: (162)..(166)
<223> OTHER INFORMATION: /label=cleavage linker /note="Ala-Leu-Asp-Pro-
      Pro linking sequence with Asp-Pro cleavage site."
<220> FEATURE:
<221> NAME/KEY: misc_feature
<222> LOCATION: (167)..(178)
<223> OTHER INFORMATION: /label=peptide sequence /note="BPI-derived
      peptide."
<220> FEATURE:
<221> NAME/KEY: misc_feature
<222> LOCATION: (600)..(610)
<223> OTHER INFORMATION: /label=XhoI /note="residues 600-610 comprise
      stop codon and XhoI site."

<400> SEQUENCE: 7
gaattcctgc aggtctatgg aacgataaat gcccatgaaa attctatttc aaggagacag        60 tcata atg aaa tac cta ttg cct acg gca gcc gct gga ttg tta tta ctc       110
      Met Lys Tyr Leu Leu Pro Thr Ala Ala Ala Gly Leu Leu Leu Leu
        1               5                  10                  15 gct gcc caa cca gcg atg gcg tcc acg ggg agc aaa cag cgc agc cag         158
Ala Ala Gln Pro Ala Met Ala Ser Thr Gly Ser Lys Gln Arg Ser Gln
              20                  25                  30 aac cgc tcc aag acg ccc aag aac cag gaa gcc ctg cgg atg gcc aac         206
Asn Arg Ser Lys Thr Pro Lys Asn Gln Glu Ala Leu Arg Met Ala Asn
         35                  40                  45 gtg gca gag aac agc agc agc gac cag agg cag gcc tgt aag aag cac         254
Val Ala Glu Asn Ser Ser Ser Asp Gln Arg Gln Ala Cys Lys Lys His
     50                  55                  60 gag ctg tat gtc agc ttc cga gac ctg ggc tgg cag gac tgg atc atc         302
Glu Leu Tyr Val Ser Phe Arg Asp Leu Gly Trp Gln Asp Trp Ile Ile
 65                  70                  75 gcg cct gaa ggc tac gcc gcc tac tac tgt gag ggg gag tgt gcc ttc         350
Ala Pro Glu Gly Tyr Ala Ala Tyr Tyr Cys Glu Gly Glu Cys Ala Phe
 80                  85                  90                  95 cct ctg aac tcc tac atg aac gcc acc aac cac gcc atc gtg cag acg         398
Pro Leu Asn Ser Tyr Met Asn Ala Thr Asn His Ala Ile Val Gln Thr
                100                 105                 110 ctg gtc cac ttc atc aac ccg gaa acg gtg ccc aag ccc tgc tgt gcg         446
Leu Val His Phe Ile Asn Pro Glu Thr Val Pro Lys Pro Cys Cys Ala
            115                 120                 125 ccc acg cag ctc aat gcc atc tcc gtc ctc tac ttc gat gac agc tcc         494
Pro Thr Gln Leu Asn Ala Ile Ser Val Leu Tyr Phe Asp Asp Ser Ser
        130                 135                 140 aac gtc atc ctg aag aaa tac aga aac atg gtg gtc cgg gcc tgt ggc         542
Asn Val Ile Leu Lys Lys Tyr Arg Asn Met Val Val Arg Ala Cys Gly
145                 150                 155 tgc cac gca ttg gat cca ccg aaa gtg ggt tgg ctg atc cag ctg ttt         590
Cys His Ala Leu Asp Pro Pro Lys Val Gly Trp Leu Ile Gln Leu Phe
160                 165                 170                 175 cat aaa aag taaagctcga g                                                610
His Lys Lys <210> SEQ ID NO 8
<211> LENGTH: 178
<212> TYPE: PRT
<213> ORGANISM: Human

<400> SEQUENCE: 8

Met Lys Tyr Leu Leu Pro Thr Ala Ala Ala Gly Leu Leu Leu Leu Ala
  1               5                  10                  15

Ala Gln Pro Ala Met Ala Ser Thr Gly Ser Lys Gln Arg Ser Gln Asn
```

```
                    20                   25                   30

Arg Ser Lys Thr Pro Lys Asn Gln Glu Ala Leu Arg Met Ala Asn Val
         35                   40                  45

Ala Glu Asn Ser Ser Ser Asp Gln Arg Gln Ala Cys Lys Lys His Glu
 50                  55                  60

Leu Tyr Val Ser Phe Arg Asp Leu Gly Trp Gln Asp Trp Ile Ile Ala
 65                  70                  75                  80

Pro Glu Gly Tyr Ala Ala Tyr Tyr Cys Glu Gly Glu Cys Ala Phe Pro
                 85                  90                  95

Leu Asn Ser Tyr Met Asn Ala Thr Asn His Ala Ile Val Gln Thr Leu
                100                 105                 110

Val His Phe Ile Asn Pro Glu Thr Val Pro Lys Pro Cys Cys Ala Pro
             115                 120                 125

Thr Gln Leu Asn Ala Ile Ser Val Leu Tyr Phe Asp Asp Ser Ser Asn
130                 135                 140

Val Ile Leu Lys Lys Tyr Arg Asn Met Val Val Arg Ala Cys Gly Cys
145                 150                 155                 160

His Ala Leu Asp Pro Pro Lys Val Gly Trp Leu Ile Gln Leu Phe His
                 165                 170                 175
Lys Lys

<210> SEQ ID NO 9
<211> LENGTH: 24
<212> TYPE: PRT
<213> ORGANISM: Human

<400> SEQUENCE: 9

Lys Trp Lys Ala Gln Phe Arg Phe Leu Lys Lys Ser Lys Val Gly Trp
 1               5                  10                  15

Leu Ile Leu Leu Phe His Lys Lys
              20

<210> SEQ ID NO 10
<211> LENGTH: 61
<212> TYPE: DNA
<213> ORGANISM: Human

<400> SEQUENCE: 10
cattggatcc accgaaatgg aaggcccagt ttcgctttct taagaaatcg aaagtgggtt    60
g                                                                    61

<210> SEQ ID NO 11
<211> LENGTH: 61
<212> TYPE: DNA
<213> ORGANISM: Human

<400> SEQUENCE: 11
ggctctcgag ctctactttt tatgaaacag caggatcagc caacccactt tcgatttctt    60
a                                                                    61

<210> SEQ ID NO 12
<211> LENGTH: 27
<212> TYPE: PRT
<213> ORGANISM: Human

<400> SEQUENCE: 12

Asp Pro Pro Lys Trp Lys Ala Gln Phe Arg Phe Leu Lys Lys Ser Lys
 1               5                  10                  15
```

Val Gly Trp Leu Ile Leu Leu Phe His Lys Lys
          20                  25

<210> SEQ ID NO 13
<211> LENGTH: 646
<212> TYPE: DNA
<213> ORGANISM: Human
<220> FEATURE:
<221> NAME/KEY: CDS
<222> LOCATION: (66)..(635)
<220> FEATURE:
<221> NAME/KEY: misc_feature
<222> LOCATION: (1)..(65)
<223> OTHER INFORMATION: /label= EcoRI /note="residues 1-65 comprise
      EcoRI site to beginning of pel B."
<220> FEATURE:
<221> NAME/KEY: misc_feature
<222> LOCATION: (1)..(22)
<223> OTHER INFORMATION: /label=pel B /note="pel B is the leader
      sequence from the pectate lyase gene of Erwinia caratovora."
<220> FEATURE:
<221> NAME/KEY: misc_feature
<222> LOCATION: (23)..(161)
<223> OTHER INFORMATION: /label= "Bone D" /note="Bone D is the subunit
      of human osteogenic protein (see, U.S. Patent No. 5,284,756 e.g.,
      Fig. 6, Example 9, Seq ID NOs: 1 and 2.'
<220> FEATURE:
<221> NAME/KEY: misc_feature
<222> LOCATION: (162)..(166)
<223> OTHER INFORMATION: /label=cleavage linker /note="Ala-Leu-Asp-Pro-
      Pro linking sequence with Asp-Pro cleavage site."
<220> FEATURE:
<221> NAME/KEY: misc_feature
<222> LOCATION: (167)..(190)
<223> OTHER INFORMATION: /label=peptide sequence /note="BPI-derived
      peptide."
<220> FEATURE:
<221> NAME/KEY: misc_feature
<222> LOCATION: (636)..(646)
<223> OTHER INFORMATION: /label=XhoI /note="residues 636-646 comprise
      stop codon and XhoI site."

<400> SEQUENCE: 13
gaattcctgc aggtctatgg aacgataaat gcccatgaaa attctatttc aaggagacag      60 tcata atg aaa tac cta ttg cct acg gca gcc gct gga ttg tta tta ctc    110
      Met Lys Tyr Leu Leu Pro Thr Ala Ala Ala Gly Leu Leu Leu Leu
       1               5                  10                  15 gct gcc caa cca gcg atg gcg tcc acg ggg agc aaa cag cgc agc cag    158
Ala Ala Gln Pro Ala Met Ala Ser Thr Gly Ser Lys Gln Arg Ser Gln
            20                  25                  30 aac cgc tcc aag acg ccc aag aac cag gaa gcc ctg cgg atg gcc aac    206
Asn Arg Ser Lys Thr Pro Lys Asn Gln Glu Ala Leu Arg Met Ala Asn
        35                  40                  45 gtg gca gag aac agc agc agc gac cag agg cag gcc tgt aag aag cac    254
Val Ala Glu Asn Ser Ser Ser Asp Gln Arg Gln Ala Cys Lys Lys His
    50                  55                  60 gag ctg tat gtc agc ttc cga gac ctg ggc tgg cag gac tgg atc atc    302
Glu Leu Tyr Val Ser Phe Arg Asp Leu Gly Trp Gln Asp Trp Ile Ile
65                  70                  75 gcg cct gaa ggc tac gcc gcc tac tac tgt gag ggg gag tgt gcc ttc    350
Ala Pro Glu Gly Tyr Ala Ala Tyr Tyr Cys Glu Gly Glu Cys Ala Phe
 80                  85                  90                  95 cct ctg aac tcc tac atg aac gcc acc aac cac gcc atc gtg cag acg    398
Pro Leu Asn Ser Tyr Met Asn Ala Thr Asn His Ala Ile Val Gln Thr
                100                 105                 110 ctg gtc cac ttc atc aac ccg gaa acg gtg ccc aag ccc tgc tgt gcg    446
Leu Val His Phe Ile Asn Pro Glu Thr Val Pro Lys Pro Cys Cys Ala
            115                 120                 125

```
ccc acg cag ctc aat gcc atc tcc gtc ctc tac ttc gat gac agc tcc    494
Pro Thr Gln Leu Asn Ala Ile Ser Val Leu Tyr Phe Asp Asp Ser Ser
        130                 135                 140 aac gtc atc ctg aag aaa tac aga aac atg gtg gtc cgg gcc tgt ggc    542
Asn Val Ile Leu Lys Lys Tyr Arg Asn Met Val Val Arg Ala Cys Gly
145                 150                 155 tgc cac gca ttg gat cca ccg aaa tgg aag gcc cag ttt cgc ttt ctt    590
Cys His Ala Leu Asp Pro Pro Lys Trp Lys Ala Gln Phe Arg Phe Leu
160                 165                 170                 175 aag aaa tcg aaa gtg ggt tgg ctg atc ctg ctg ttt cat aaa aag        635
Lys Lys Ser Lys Val Gly Trp Leu Ile Leu Leu Phe His Lys Lys
                180                 185                 190 tagagctcga g                                                       646
```

<210> SEQ ID NO 14
<211> LENGTH: 190
<212> TYPE: PRT
<213> ORGANISM: Human

<400> SEQUENCE: 14

```
Met Lys Tyr Leu Leu Pro Thr Ala Ala Gly Leu Leu Leu Leu Ala
  1               5                  10                  15

Ala Gln Pro Ala Met Ala Ser Thr Gly Ser Lys Gln Arg Ser Gln Asn
                 20                  25                  30

Arg Ser Lys Thr Pro Lys Asn Gln Glu Ala Leu Arg Met Ala Asn Val
             35                  40                  45

Ala Glu Asn Ser Ser Ser Asp Gln Arg Gln Ala Cys Lys Lys His Glu
 50                  55                  60

Leu Tyr Val Ser Phe Arg Asp Leu Gly Trp Gln Asp Trp Ile Ile Ala
 65                  70                  75                  80

Pro Glu Gly Tyr Ala Ala Tyr Tyr Cys Glu Gly Glu Cys Ala Phe Pro
                 85                  90                  95

Leu Asn Ser Tyr Met Asn Ala Thr Asn His Ala Ile Val Gln Thr Leu
            100                 105                 110

Val His Phe Ile Asn Pro Glu Thr Val Pro Lys Pro Cys Cys Ala Pro
        115                 120                 125

Thr Gln Leu Asn Ala Ile Ser Val Leu Tyr Phe Asp Asp Ser Ser Asn
    130                 135                 140

Val Ile Leu Lys Lys Tyr Arg Asn Met Val Val Arg Ala Cys Gly Cys
145                 150                 155                 160

His Ala Leu Asp Pro Pro Lys Trp Lys Ala Gln Phe Arg Phe Leu Lys
                165                 170                 175

Lys Ser Lys Val Gly Trp Leu Ile Leu Leu Phe His Lys Lys
            180                 185                 190
```

<210> SEQ ID NO 15
<211> LENGTH: 1813
<212> TYPE: DNA
<213> ORGANISM: Human
<220> FEATURE:
<221> NAME/KEY: CDS
<222> LOCATION: (31)..(1491)
<220> FEATURE:
<221> NAME/KEY: mat_peptide
<222> LOCATION: (124)..(1491)
<220> FEATURE:
<223> OTHER INFORMATION: "rBPI"

<400> SEQUENCE: 15
caggccttga ggttttggca gctctggagg atg aga gag aac atg gcc agg ggc    54

-continued

```
                    Met Arg Glu Asn Met Ala Arg Gly
                        -30                 -25
cct tgc aac gcg ccg aga tgg gtg tcc ctg atg gtg ctc gtc gcc ata      102
Pro Cys Asn Ala Pro Arg Trp Val Ser Leu Met Val Leu Val Ala Ile
        -20             -15                 -10 ggc acc gcc gtg aca gcg gcc gtc aac cct ggc gtc gtg gtc agg atc      150
Gly Thr Ala Val Thr Ala Ala Val Asn Pro Gly Val Val Val Arg Ile
        -5              -1  1                   5 tcc cag aag ggc ctg gac tac gcc agc cag cag ggg acg gcc gct ctg      198
Ser Gln Lys Gly Leu Asp Tyr Ala Ser Gln Gln Gly Thr Ala Ala Leu
 10              15                  20                      25 cag aag gag ctg aag agg atc aag att cct gac tac tca gac agc ttt      246
Gln Lys Glu Leu Lys Arg Ile Lys Ile Pro Asp Tyr Ser Asp Ser Phe
                 30                  35                  40 aag atc aag cat ctt ggg aag ggg cat tat agc ttc tac agc atg gac      294
Lys Ile Lys His Leu Gly Lys Gly His Tyr Ser Phe Tyr Ser Met Asp
                 45                  50                  55 atc cgt gaa ttc cag ctt ccc agt tcc cag ata agc atg gtg ccc aat      342
Ile Arg Glu Phe Gln Leu Pro Ser Ser Gln Ile Ser Met Val Pro Asn
             60                  65                  70 gtg ggc ctt aag ttc tcc atc agc aac gcc aat atc aag atc agc ggg      390
Val Gly Leu Lys Phe Ser Ile Ser Asn Ala Asn Ile Lys Ile Ser Gly
         75                  80                  85 aaa tgg aag gca caa aag aga ttc tta aaa atg agc ggc aat ttt gac      438
Lys Trp Lys Ala Gln Lys Arg Phe Leu Lys Met Ser Gly Asn Phe Asp
 90                  95                 100                 105 ctg agc ata gaa ggc atg tcc att tcg gct gat ctg aag ctg ggc agt      486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc      534
Asn Pro Thr Ser Gly Lys Pro Thr Ile Thr Cys Ser Ser Cys Ser Ser
                125                 130                 135 cac atc aac agt gtc cac gtg cac atc tca aag agc aaa gtc ggg tgg      582
His Ile Asn Ser Val His Val His Ile Ser Lys Ser Lys Val Gly Trp
            140                 145                 150 ctg atc caa ctc ttc cac aaa aaa att gag tct gcg ctt cga aac aag      630
Leu Ile Gln Leu Phe His Lys Lys Ile Glu Ser Ala Leu Arg Asn Lys
 155                 160                 165 atg aac agc cag gtc tgc gag aaa gtg acc aat tct gta tcc tcc aag      678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct      726
Leu Gln Pro Tyr Phe Gln Thr Leu Pro Val Met Thr Lys Ile Asp Ser
                190                 195                 200 gtg gct gga atc aac tat ggt ctg gtg gca cct cca gca acc acg gct      774
Val Ala Gly Ile Asn Tyr Gly Leu Val Ala Pro Pro Ala Thr Thr Ala
            205                 210                 215 gag acc ctg gat gta cag atg aag ggg gag ttt tac agt gag aac cac      822
Glu Thr Leu Asp Val Gln Met Lys Gly Glu Phe Tyr Ser Glu Asn His
        220                 225                 230 cac aat cca cct ccc ttt gct cca cca gtg atg gag ttt ccc gct gcc      870
His Asn Pro Pro Pro Phe Ala Pro Pro Val Met Glu Phe Pro Ala Ala
    235                 240                 245 cat gac cgc atg gta tac ctg ggc ctc tca gac tac ttc ttc aac aca      918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga      966
Ala Gly Leu Val Tyr Gln Glu Ala Gly Val Leu Lys Met Thr Leu Arg
                270                 275                 280
```

-continued

```
gat gac atg att cca aag gag tcc aaa ttt cga ctg aca acc aag ttc       1014
Asp Asp Met Ile Pro Lys Glu Ser Lys Phe Arg Leu Thr Thr Lys Phe
        285                 290                 295 ttt gga acc ttc cta cct gag gtg gcc aag aag ttt ccc aac atg aag       1062
Phe Gly Thr Phe Leu Pro Glu Val Ala Lys Lys Phe Pro Asn Met Lys
    300                 305                 310 ata cag atc cat gtc tca gcc tcc acc ccg cca cac ctg tct gtg cag       1110
Ile Gln Ile His Val Ser Ala Ser Thr Pro Pro His Leu Ser Val Gln
315                 320                 325 ccc acc ggc ctt acc ttc tac cct gcc gtg gat gtc cag gcc ttt gcc       1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac       1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga       1254
Thr Thr Gly Ser Met Glu Val Ser Ala Glu Ser Asn Arg Leu Val Gly
            365                 370                 375 gag ctc aag ctg gat agg ctg ctc ctg gaa ctg aag cac tca aat att       1302
Glu Leu Lys Leu Asp Arg Leu Leu Leu Glu Leu Lys His Ser Asn Ile
        380                 385                 390 ggc ccc ttc ccg gtt gaa ttg ctg cag gat atc atg aac tac att gta       1350
Gly Pro Phe Pro Val Glu Leu Leu Gln Asp Ile Met Asn Tyr Ile Val
    395                 400                 405 ccc att ctt gtg ctg ccc agg gtt aac gag aaa cta cag aaa ggc ttc       1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag       1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa           1491
Pro His Gln Asn Phe Leu Leu Phe Gly Ala Asp Val Val Tyr Lys
            445                 450                 455 tgaaggcacc agggtgccg gggctgtca gccgcacctg ttcctgatgg gctgtggggc       1551
accggctgcc tttcccagg gaatcctctc cagatcttaa ccaagagccc cttgcaaact       1611
tcttcgactc agattcagaa atgatctaaa cacgaggaaa cattattcat tggaaaagtg      1671
catggtgtgt attttaggga ttatgagctt ctttcaaggg ctaaggctgc agagatattt      1731
cctccaggaa tcgtgtttca attgtaacca agaaatttcc atttgtgctt catgaaaaaa     1791
aacttctggt tttttttcatg tg                                              1813
```

<210> SEQ ID NO 16
<211> LENGTH: 487
<212> TYPE: PRT
<213> ORGANISM: Human

<400> SEQUENCE: 16

```
Met Arg Glu Asn Met Ala Arg Gly Pro Cys Asn Ala Pro Arg Trp Val
        -30                 -25                 -20

Ser Leu Met Val Leu Val Ala Ile Gly Thr Ala Val Thr Ala Ala Val
-15                 -10                 -5                  -1   1

Asn Pro Gly Val Val Val Arg Ile Ser Gln Lys Gly Leu Asp Tyr Ala
                5                   10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45
```

-continued

```
His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
        340                 345                 350

Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
        420                 425                 430

Gln Leu Tyr Asn Val Val Leu Gln Pro His Gln Asn Phe Leu Leu Phe
    435                 440                 445

Gly Ala Asp Val Val Tyr Lys
450                 455
```

METHODS FOR RECOMBINANT PEPTIDE PRODUCTION

This application is a continuation of U.S. application Ser. No. 09/760,397, filed Jan. 12, 2001, now U.S. Pat. No. 6,500,648, which is a continuation of U.S. application Ser. No. 09/271,970, filed Mar. 18, 1999, now U.S. Pat. No. 6,242,219.

The present invention relates generally to improved methods for the production of recombinant peptides from bacterial cells.

BACKGROUND OF THE INVENTION

Although bioactive peptides can be produced chemically by a variety of synthesis strategies, recombinant production of peptides, including those in the 5-50 amino acid size range, offers the potential for large scale production at reasonable cost. However, expression of very short polypeptide chains can sometimes be problematic in microbial systems, including in bacterial cells such as *Escherichia coli*. This is true even when the peptide sequence is expressed as part of a fusion protein. As part of a fusion protein, peptides may be directed to specific cellular compartments, i.e. cytoplasm, periplasm, or media, with the goal of achieving high expression yield and avoiding cellular degradative processes.

Preparation of a peptide from a fusion protein in pure form requires that the peptide be released and recovered from the fusion protein by some mechanism and then obtained by isolation or purification. Methods for cleaving fusion proteins have been identified. Each method recognizes a chemical or enzymatic cleavage site that links the carrier protein to the desired protein or peptide [Forsberg et al., *I. J. Protein Chem.* 11, 201-211, (1992)]. Chemical cleavage reagents in general recognize single or paired amino acid residues which may occur at multiple sites along the primary sequence, and therefore may be of limited utility for release of large peptides or protein domains which contain multiple internal recognition sites. However, recognition sites for chemical cleavage can be useful at the junction of short peptides and carrier proteins. Chemical cleavage reagents include cyanogen bromide, which cleaves at methionine residues [Piers et al., *Gene,* 134, 7, (1993)], N-chloro succinimide [Forsberg et al., *Biofactors* 2, 105-112, (1989)] or BNPS-skatole [Knott et al., *Eur. J. Biochem.* 174, 405-410, (1988); Dykes et al., *Eur. J. Biochem.* 174, 411-416, (1988)] which cleaves at tryptophan residues, dilute acid which cleaves aspartyl-prolyl bonds [Gram et al., *Bio/Technology* 12, 1017-1023, (1994); Marcus, *Int. J. Peptide Protein Res.,* 25, 542-546, (1985)], and hydroxylamine which cleaves asparagine-glycine bonds at pH 9.0 [Moks et al., *Bio/Technology* 5, 379-382, (1987)].

Of interest is U.S. Pat. No. 5,851,802 which describes a series of recombinant peptide expression vectors that encode peptide sequences derived from bactericidal/permeability-increasing protein (BPI) linked via amino acid cleavage site sequences as fusions to carrier protein sequences. In some fusion protein constructs, an acid labile aspartyl-prolyl bond was positioned at the junction between the peptide and carrier protein sequences. BPI-derived peptides were released from the fusion proteins by dilute acid treatment of isolated inclusion bodies without prior solubilization of the inclusion bodies. The released peptides were soluble in the aqueous acidic environment. In addition, BPI-derived peptides were obtained from fusion proteins under conditions where the fusion proteins were secreted into the culture medium. Those secreted fusion proteins were then purified and treated with dilute acid to release the peptide.

Of additional interest are the disclosures of the following references which relate to recombinant fusion proteins and peptides.

Shen, *Proc. Nat'l. Acad. Sci. (USA),* 281, 4627 (1984) describes bacterial expression as insoluble inclusion bodies of a fusion protein encoding pro-insulin and β-galactosidase; the inclusion bodies were first isolated and then solubilized with formic acid prior to cleavage with cyanogen bromide.

Kempe et al., *Gene,* 39, 239 (1985) describes expression as insoluble inclusion bodies in *E. coli* of a fusion protein encoding multiple units of neuropeptide substance P and β-galactosidase; the inclusion bodies were first isolated and then solubilized with formic acid prior to cleavage with cyanogen bromide.

Lennick et al., *Gene,* 61, 103 (1987) describes expression as insoluble inclusion bodies in *E. coli* of a fusion protein encoding multiple units (8) of α-human atrial natriuretic peptide; the inclusion bodies were first isolated and then solubilized with urea prior to endoproteinase cleavage.

Dykes et al., *Eur. J. Biochem.,* 174, 411 (1988) describes soluble intracellular expression in *E. coli* of a fusion protein encoding α-human atrial natriuretic peptide and chloramphenicol acetyltransferase; the fusion protein was proteolytically cleaved or chemically cleaved with 2-(2-nitrophenyl-sulphenyl)-E-methyl-3'-bromoindolenine to release peptide.

Ray et al., *Bio/Technology,* 11, 64 (1993) describes soluble intracellular expression in *E. coli* of a fusion protein encoding salmon calcitonin and glutathione-S-transferase; the fusion protein was cleaved with cyanogen bromide.

Schellenberger et al., *Int. J. Peptide Protein Res.,* 41, 326 (1993) describes expression as insoluble inclusion bodies of a fusion protein encoding a substance P peptide (11a.a.) and β-galactosidase; the inclusion bodies were first isolated and then treated with chymotrypsin to cleave the fusion protein.

Hancock et al., WO94/04688 (PCT/CA93/00342) and Piers et al. (Hancock), *Gene,* 134, 7 (1993) describe (a) expression as insoluble inclusion bodies in *E. coli* of a fusion protein encoding a defensin peptide designated human neutrophil peptide 1 (HNP-1) or a hybrid cecropin/mellitin (CEME) peptide and glutathione-5-transferase (GST); the inclusion bodies were first isolated and then: (i) extracted with 3% octyl-polyoxyethylene prior to urea solubilization and prior to factor $X_a$ protease for HNP1-GST fusion protein or (ii) solubilized with formic acid prior to cyanogen bromide cleavage for CEME-GST fusion protein; (b) expression in the extracellular supernatant of *S. aureus* of a fusion protein encoding CEME peptide and protein A; (c) proteolytic degradation of certain fusion proteins with some fusion protein purified; and (d) proteolytic degradation of other fusion proteins and inability to recover and purify the fusion protein.

Lai et al., U.S. Pat. No. 5,206,154 and Callaway, Lai et al. *Antimicrob. Agents & Chemo.,* 37:1614 (1993) describe expression as insoluble inclusion bodies of a fusion protein encoding a cecropin peptide and the protein encoded by the 5'-end of the L-ribulokinase gene; the inclusion bodies were first isolated and then solubilized with formic acid prior to cleavage with cyanogen bromide.

Gramm et al., *Bio/Technology,* 12:1017 (1994) describes expression as insoluble inclusion bodies in *E. coli* of a fusion protein encoding a human parathyroid hormone peptide and a bacteriophage T4-encoded gp55 protein; the inclusion bodies were first isolated (6% wt/vol.) and then were treated with acid to hydrolyze the Asp-Pro cleavage site.

Kuliopulos et al., *J. Am. Chem. Soc.*, 116:4599 (1994) describes expression as insoluble inclusion bodies in *E. coli* of a fusion protein encoding multiple units of a yeast α-mating type peptide and a bacterial ketosteroid isomerase protein; the inclusion bodies were first isolated and then solubilized with guanidine prior to cyanogen bromide cleavage.

Pilon et al., *Biotechnol. Prog.*, 13, 374-379 (1997) describe soluble intracellular expression in *E. coli* of a fusion protein encoding a peptide and ubiquitin; the fusion protein was cleaved with a ubiquitin specific protease, UCH-L3.

Haught et al., *Biotechnol. Bioengineer.*, 57, 55-61 (1998) describe expression as insoluble inclusion bodies in *E. coli* of a fusion protein encoding an antimicrobial peptide designated P2 and bovine prochymosin; the inclusion bodies were first isolated and then solubilized with formic acid prior to cleavage with cyanogen bromide.

The above-references indicate that production of small peptides from bacteria has been problematic for a variety of reasons. Proteolysis of some peptides has been particularly problematic, even where the peptide is made as a part of a larger fusion protein. Such fusion proteins comprising a carrier protein/peptide may not be expressed by bacterial host cells or may be expressed but cleaved by bacterial proteases. In particular, difficulties in expressing cationic antimicrobial peptides in bacteria have been described by Hancock et al. WO94/04688 (PCT/CA93/00342) referenced above, due in their view to the susceptibility of such polycationic peptides to bacterial protease degradation.

The production of peptide for preclinical and clinical evaluation often requires multigram quantities [Kelley, *Bio/Technology* 14, 28-31 (1996)]. If production of recombinant peptides can be achieved at this large scale, such production can potentially be economical. However, downstream processing steps for the production of peptides and proteins from bacteria can often contribute a significant fraction of total production cost. Initial recovery of peptide from bacterial inclusion bodies of fusion proteins, for-example, generally requires multiple distinct processing steps, including the following four steps: (1) cell disruption/lysis, (2) isolation of inclusion bodies from the disrupted/lysed cells, (3) solubilization of the isolated inclusion bodies in denaturant or detergent to obtain solubilized fusion protein, and (4) fusion protein cleavage and separation of peptide and carrier protein. It is desirable that aspects of the recombinant production process be improved and/or optimized in order to make large-scale production of peptides by recombinant means more economically viable.

There continues to exist a need in the art for improved methods for recombinant production of peptides from bacterial cells, particularly for simpler methods that do not require a multiplicity of steps, including, for example, the step of isolation or purification of peptide fusion proteins or the step of isolation or purification of inclusion bodies comprising the fusion proteins in order to obtain the recombinant peptide.

SUMMARY OF THE INVENTION

The present invention provides improved methods for the production of recombinant peptides from bacterial cells. The improved methods preclude the need for the isolation and solubilization of inclusion bodies or the isolation and purification of peptide fusion proteins. The improved methods accomplish cell disruption/lysis and release of peptide from bacterial cells or bacterial cell cultures in a single step.

Fusion proteins useful in methods of the invention comprise at least one peptide sequence, a carrier protein sequence, and at least one acid-sensitive amino acid cleavage site sequence located between the peptide sequence and the carrier protein sequence. The invention provides improved methods for the microbial production of peptides from such fusion proteins expressed intracellularly in bacterial cells. The recombinant peptides recovered according to the invention are released by acid cleavage at the acid-sensitive cleavage site(s) in the fusion protein. Recombinant peptides are thus efficiently and economically produced according to the invention.

The invention thus provides an improved method for obtaining a peptide from bacterial cells after expression inside the cells of a fusion protein, wherein the fusion protein comprises the peptide, a carrier protein and an acid-cleavable site between the peptide and the carrier protein, with the improvement comprising treating the bacterial cells with acid under conditions sufficient in a single step to disrupt or lyse the cells and release the peptide from the fusion protein. An improved method may include the additional step of obtaining the released peptide separated from the disrupted or lysed cells. According to the invention, the released peptide may be separated from the disrupted or lysed cells by a separation device, such as a centrifugation device or a filtration device. The invention also provides an improved method for obtaining a peptide from bacterial cells after expression inside the cells of a fusion protein, wherein the fusion protein comprises the peptide, a carrier protein and an acid-cleavable site between the peptide and the carrier protein with the improvement comprising the following steps: (a) treating the bacterial cells with acid under conditions sufficient to disrupt or lyse the cells and release the peptide from the fusion protein; (b) separating soluble material from insoluble material after step (a); and (c) recovering the released peptide in the soluble material after step (b). According to the invention, the soluble material may be separated from the insoluble material by a separation device, such as a centrifugation device or a filtration device. Improved methods of the invention may be employed where the bacterial cells are in cell culture media for the acid treatment, or where the bacterial cells have been separated from cell culture media for the acid treatment, or where the bacterial cells are in cell culture media in a fermentation vessel for the acid treatment. According to methods of the invention, preferred acid-cleavable sites in the fusion protein include an Asp-Pro cleavage site. Preferably, the carrier protein is expressed as an insoluble protein inside the bacterial cells.

Improved methods of the invention for recombinant microbial production of peptides from fusion proteins are based on the surprising discovery that bacterial cell disruption/lysis and peptide release may be accomplished simultaneously in a single step. According to the invention, no process step is required for the isolation from the cells of inclusion bodies and solubilization of such inclusion bodies prior to peptide release and recovery. Similarly, no process step is required for the purification of the fusion proteins expressed in large amounts intracellularly as soluble or insoluble proteins in bacterial host cells prior to peptide release and recovery. Remarkably, peptides efficiently produced as components of fusion proteins by the bacterial host cells are efficiently cleaved and released from the fusion proteins by a single step of cell disruption/lysis and peptide release. It is particularly surprising that peptides according to the invention effectively made in *E. coli* are released in soluble form in this single step of cell disruption/lysis and peptide cleavage and are easily recovered from insoluble cell material. By way of example, recombinant BPI-derived peptides having one or more of the biological activities of BPI (e.g., LPS binding, LPS neutralization, heparin binding, heparin neutralization, antimicrobial activity) have been produced and recovered according to the methods of invention. Thus, the invention provides improved methods of bacterial cell production of functional recombinant peptides.

DETAILED DESCRIPTION

The present invention provides improved recombinant peptide production methods. Recombinant peptides encoded by and released from fusion proteins are recovered according to these improved methods. Fusion proteins useful in methods according to the invention comprise a peptide sequence, a carrier protein sequence and an acid-sensitive amino acid cleavage site sequence between the peptide and carrier protein sequences. Improved methods according to the invention accomplish cell disruption/lysis and release of peptide from the cells in a single step using bacterial cells or bacterial cell cultures (e.g., fermentation cultures). The methods preclude the need for disruption/lysis followed by isolation and solubilization of inclusion bodies of the fusion proteins from the bacterial cells prior to peptide release and recovery. Unexpectedly, single step treatment of bacterial cells or bacterial cell cultures under conditions of acid pH and temperature sufficient to cleave and release peptides simultaneous with cell disruption/lysis, allows the direct recovery of soluble peptide from insoluble cell lysis material. Fusion proteins containing BPI-derived peptides with anti-microbial activity were expressed intracellularly in large amounts without significant proteolysis, until acidification of the bacterial cells. A variety of BPI-derived peptides, including those comprising the sequences listed in Table 4 of U.S. Pat. No. 5,851,802 incorporated by reference herein in its entirety, may be produced by recombinant methods according to the invention.

An advantage provided by the present invention is the ability to produce peptides from fusion proteins more efficiently and economically from bacterial host cells. Additional advantages include the ability to recover and obtain homogeneous peptide in large amounts via improved methods that are particularly amenable to scale-up in large fermentation vessels.

"BPI-derived peptide" or "BPI peptide" as used herein refers to a peptide derived from or based on bactericidal/permeability-increasing protein (BPI), including peptides derived from Domain I (amino acids 17-45), Domain II (amino acids 65-99) and Domain III (amino acids 142-169) of BPI (SEQ ID NOS: 15 and 16), each peptide having an amino acid sequence that is the amino acid sequence of a BPI functional domain or a subsequence thereof and variants of the sequence or subsequence having at least one of the biological activities of BPI. The amino acid sequence of the entire human BPI protein and the nucleic acid sequence of DNA encoding the protein have been reported in FIG. 1 of Gray et al., *J. Biol. Chem.*, 264, 9505 (1989), incorporated herein by reference. The Gray et al. DNA and amino acid sequences are set out in SEQ ID NOS: 15 and 16 hereto. An N-terminal BPI fragment of approximately 23 kD, referred to as rBPI$_{23}$, [Gazzano-Santoro et al., *Infect. Immun.* 60, 4754-4761 (1992)], an analog designated rBPI$_{21}$ or rBPI$_{21}$Δcys (U.S. Pat. No. 5,420,019, incorporated by reference herein) as well as recombinant holoprotein, also referred to as rBPI, have been produced having sequences set out in SEQ ID NOS: 15 and 16, except that valine at position 151 is specified by GTG rather than GTC and residue 185 is glutamic acid (specified by GAG) rather than lysine (specified by AAG). As used herein, a "biological activity of BPI" refers to LPS binding, LPS neutralization, heparin binding, heparin neutralization or antimicrobial activity (including anti-bacterial and anti-fungal activity). Such BPI-derived peptides having at least one of the activities of BPI may be useful as antimicrobial agents (including anti-bacterial and anti-fungal agents), as endotoxin binding and neutralizing agents, and as heparin binding and neutralizing agents including agents for neutralizing the anticoagulant effects of administered heparin, for treatment of chronic inflammatory disease states, and for inhibition of normal or pathological angiogenesis. "Cationic BPI peptide" refers to a BPI peptide with a pI>7.0.

As used herein a "transformed bacterial host cell refers to a bacterial cell that contains recombinant genetic material or a bacterial cell that contains genetic material required for expression of a recombinant product. The genetic material may be introduced by any method known in the art including transformation, transduction, electroporation and infection.

As used herein, a "vector" or "vector construct" refers to plasmid DNA that contains recombinant genetic material which may encode a recombinant product(s) and may be capable of autonomous replication in bacteria.

"Carrier protein" as used herein refers to a protein that can be expressed in bacteria and used as a fusion partner to a linked peptide or protein. Preferred carrier proteins are those that can be expressed at high yield and when used as a fusion partner can confer high level-expression to a linked peptide or protein. Particularly preferred carrier proteins are those that are expressed intracellularly as soluble or insoluble proteins, such as the D subunit of a human osteogenic protein ("Bone D"). Any known carrier protein may be utilized as a protein fusion partner, including, for example, ubiquitin, [see e.g., Pilon et al., *Biotechol. Prog.* 13, 374-379 (1997)]; staphylococcal protein A, [see e.g., Uhlén et al., *Gene* 23, 369:378 (1983) and Piers et al., *Gene* 134, 7-13 (1993)]; thioredoxin, [see e.g., LaVallie et al., *Bio/Technology* 11, 187-193 (1993)]; maltose binding protein, [see e.g., Tsao et al., *Gene* 169, 59-64 (1996)]; glutathione-s-transferase, [see e.g., Ray et al., *Bio/Technoloty* 11 64-70 (1993) and Piers et al., *Gene* 134, 7-13 (1993)]; prochymosin, [see e.g., Haught et al., *Biotechnology and Bioengineering* 57, 55-61 (1998)]; β-galactosidase, [see e.g., Kempe et al., *Gene* 39, 239-245 (1985)]; and gp 55 from T4, [see e.g., Gram et al., *Bio/Technology* 12, 1017-1023 (1994)]. A "cationic carrier protein" as used herein refers to a carrier protein having a pI (as calculated based on amino acid sequence or as measured in solution) greater than 7.0 and preferably greater than 8.0. Such proteins include (1) Bone D (pI 8.18) (SEQ ID NOS: 1 and 2) and (2) gelonin (pI 9.58) (see, e.g., U.S. Pat. Nos. 5,416,202 and 5,851,802, hereby incorporated by reference in their entirety).

"Amino acid cleavage site" as used herein refers to an amino acid or amino acids that serve as a recognition site for a chemical or enzymatic reaction such that the peptide chain is cleaved at that site by the chemical agent or enzyme. Amino acid cleavage sites include those at aspartic acid-proline (Asp-Pro), methionine (Met), tryptophan (Trp) or glutamic acid (Glu). "Acid-sensitive amino acid cleavage site" as used herein refers to an amino acid or amino acids that serve as a recognition site such that the peptide chain is cleaved at that site by acid. Particularly preferred is the Asp-Pro cleavage site which may be cleaved between Asp and Pro by acid hydrolysis.

Peptides derived from or based on BPI (BPI-derived peptides), are described in co-owned U.S. Pat. No. 5,858, 974 [WO 97/04008 (PCT/US96/03845)]; U.S. patent application Ser. Nos. 08/504,841 and 09/119,858 [WO 96/08509 (PCT/US95/09262)]; U.S. Pat. Nos. 5,652,332 and 5,856,438 [WO 95/19372 (PCT/US94/10427)]; U.S. Pat. Nos. 5,733,872 and 5,763,567 [WO 94/20532 (PCT/US94/02465)]; U.S. Pat. Nos. 4,348,942; 5,639,727; 5,807,818; 5,837,678; and 5,854,214 [WO 94/20128 (PCT/US94/02401)]; the disclosures of all of which are incorporated herein by reference.

Other aspects and advantages of the present invention will be understood upon consideration of the following illustrative examples wherein Example 1 addresses construction of fusion protein expression vector constructs; Example 2 addresses expression of recombinant fusion proteins; Example 3 addresses acid hydrolysis of bacterial cells or bacterial cell cultures and release of recombinant peptide; Example 4 addresses acid hydrolysis of bacterial cell cultures in fermentation vessels; Example 5 addresses acid hydrolysis of bacterial cells after removal of cell culture medium; Example 6 addresses recovery and purification of recombinant peptides from acid hydrolyzed bacterial cells; and Example 7 addresses biological activity assays of recombinant peptides.

EXAMPLE 1

Construction of Fusion Protein Expression Vectors

1. Bacterial Expression Vector Construct pING4702

A bacterial expression vector which would encode a peptide fusion protein, was constructed. This vector contains a sequence for a gene encoding subunit D of a human osteogenic protein ("Bone D") (see, amino acids 23 through 161 of SEQ ID NOS: 1 and 2), linked to a sequence encoding a linking sequence that includes the dipeptide Asp-Pro and a sequence encoding a peptide derived from the sequence of BPI (SEQ ID NO: 3). This vector construct, pING4702, was prepared in several steps as described below.

First, two synthetic oligonucleotides were synthesized that encode a BPI-derived peptide, an Asp-Pro dipeptide and appropriate restriction enzyme recognition sites for cloning. The oligonucleotides encoding this sequence were:

The annealed oligonucleotide fragment also contains restriction enzyme sites for cleavage by BamHI at the 5' end and XhoI at the 3' end of sequence. The resulting annealed oligonucleotide was purified by centrifugation on a Chroma Spin 10 column (Clontech, Palo Alto, Calif.).

Second, DNA fragments from two plasmid vectors were prepared. Plasmid pIC100, a derivative of pBR322 and which includes the leader sequence of the *E. carotovora* pelB gene, described in U.S. Pat. No. 5,416,202 (see, e.g., Example 10) incorporated by reference, was digested with EcoRI and XhoI, and the large vector fragment of approximately 2836 bp, was purified. Plasmid pING3353, described in U.S. Pat. No. 5,851,802, incorporated by reference, was digested with EcoRI and BamHI and the approximately 550 bp fragment which encodes the pelB:Bone D protein was purified.

Third, the annealed oligonucleotide, the EcoRI to XhoI fragment from pING100 and the EcoRI to BamHI fragment from pING3353 were ligated in 20 µL 50 mM Tris, pH 7.6, 10 mM MgCl$_2$, 1 mM ATP, 1 mM DTT, 5% PEG-8000 with 3 Units T4 DNA Ligase for 16 hours at 4° C. to generate the intermediate vector pING4700. Plasmid pING4700 confers ampicillin resistance and encodes the fusion protein Bone D-Asp-Pro-peptide.

Plasmid pING4700 was digested with EcoRI and XhoI, and the 604 bp fragment encoding the fusion protein was ligated to the approximately 5500 bp vector fragment from pING3217, as described in U.S. Pat. No. 5,851,802, (see Example 1), that had been digested with EcoRI and XhoI in µL 50 mM Tris, pH 7.6, 10 MM MgCl$_2$, 1 mM ATP, 1 mM DTT, 5% PEG-8000 with 3 Units T4 DNA Ligase for 16 hours at 4° C. The resulting plasmid, pING4702, encodes the Bone D-Asp-Pro-Pro-peptide fusion protein (SEQ ID NOS: 7 and 8) under the transcriptional control of the araB promoter. Plasmid pING4702 confers resistance to the antibiotic tetracycline.

2. Bacterial Expression Vector Construct pING4703

A second bacterial expression vector was constructed which encodes a peptide fusion protein containing Bone D (see, amino acid 23 through 161 of SEQ ID NOS: 1 and 2), the dipeptide Asp-Pro and a 25 amino acid peptide derived from the sequence of BPI (SEQ ID NO: 9). This vector construct, pING4703, was prepared as described below.

```
5'-GATCCACCGAAAGTGGGTTGGCTGATCCAGCTGTTCCACAAAAAGTAAAGC-3'   (SEQ ID NO: 4)

5'-TCGAGCTTTACTTTTTGTGGAACAGCTGGATCAGCCAACCCACTTTCGGTG-3'   (SEQ ID NO: 5)
```

Sixteen µg of each oligonucleotide were annealed in a 50 µL reaction in 100 mM NaCl, 10 mM Tris, pH 7.8, 1 mM EDTA for 10 minutes at 68° C., 30 minutes at 57° C., and followed by slow cooling to room temperature. The resulting annealed oligonucleotide fragment encodes an Asp-Pro-Pro sequence followed by sequence encoding a peptide with the 12 amino acid sequence of XMP.391, as described in U.S. Pat. No. 5,851,802:

Asp Pro Pro Lys Val Gly Trp Leu Ile Gln Leu Phe His Lys Lys (SEQ ID NO: 6)

First, two synthetic oligonucleotides were synthesized that encode a BPI-derived peptide, an Asp-Pro-Pro sequence and appropriate restriction enzyme recognition sites for cloning. The oligonucleotides encoding this sequence were:

```
5'- CATTGGATCCACCGAAATGGAAGGCCCAGTTTCGCTTTCTTAAGAAA TCGAAAGTGGGTTG -3'   (SEQ ID NO: 10)

5'- GGCTCTCGAGCTCTACTTTTTATGAAACAGCAGGATCAGCCAACCCACTTTCGATTTCTTA -3'   (SEQ ID NO: 11)
```

Sixteen µg of each oligonucleotide were annealed in a 50 µL reaction. in 100 mM NaCl, 10 mM Tris, pH 7.8, 1 mM EDTA for 10 minutes at 68° C., 30 minutes at 57° C., followed by slow cooling to room temperature. An aliquot of the annealed oligonucleotides was diluted into 10 mM Tris, pH 8.3, 50 mM KCl (300 µL total volume) and filled-in with a reaction containing AmpliTaq (Perkin Elmer, Norwalk, Conn.), dATP, dGTP, dCTP and dTTP at 72° C. The resulting double-stranded fragment encoded the restriction sites BamHI and XhoI at the 5' and 3' ends, respectively, and encoded an Asp-Pro-Pro sequence followed by a sequence encoding a peptide with the 24 amino sequence of XMP.102, as described in U.S. Pat. No. 5,851,802:

Asp Pro Pro Lys Trp Lys Ala Gln Phe Arg Phe Leu Lys Lys Ser Lys Val Gly Trp Leu Ile Leu Leu Phe His Lys Lys (SEQ ID NO: 12)

The double-stranded fragment was digested with BamHI and XhoI, and ligated to both the approximately 5500 bp EcoRI to XhoI vector fragment from pING3217, and the approximately 550 bp EcoRI to BamHI fragment of pING3353 in 20 µL 50 mM Tris, pH 7.6, 10 mM $MgCl_2$, 1 mM ATP, 1 mM dithiothreitol, 5% PEG-8000 with 1 Unit T4 DNA Ligase for 16 hours at 4° C. The resulting plasmid, pING4703, encodes the Bone D-Asp-Pro-Pro-peptide fusion protein (SEQ ID NOS: 13 and 14) under the transcriptional control of the araB promoter. Plasmid pING4703 confers resistance to the antibiotic tetracycline.

EXAMPLE 2

Expression of Recombinant Fusion Proteins

Expression of a recombinant product under control of the araB promoter was evaluated as follows. Expression vector constructs were transformed into *E. coli* E104 (deposited as ATCC 69009; ATCC 69008; ATCC 69101; ATCC 69102; ATCC 69103; ATCC 69104; ATCC 69331; ATCC 69332; ATCC 69333, each containing a gelonin-encoding plasmid) and tetracycline resistant colonies were selected. Bacterial cultures from these colonies were grown at 37° C. in TYE medium (15 g Tryptone, 10 g Yeast Extract, 5 g NaCl per liter) supplemented with 15 µg/mL of tetracycline. For storage of bacterial cells prior to growth in a fermentor, bacterial cultures (1 to 2 mL) were frozen in TYE medium supplemented with 15% glycerol and stored at −20° C. To initiate production of recombinant product, a vial of cells containing the product expression vector was thawed, and inoculated into 100 mL of GMM culture medium as described below and grown to approximately 200 Klett Units, then inoculated into either a 14 L or 35 L fermentor. Each fermentor contained a minimal salts medium with glycerol as a carbon source (Glycerol Minimal Medium, GMM). The 14 L or 35 L fermentor vessel initially contained approximately 7 L or 20 L, respectively, of GMM which contains the following ingredients per liter:

| Autoclaved Ingredients | |
|---|---|
| $(NH_4)_2SO_4$ | 12 g |
| $KH_2PO_4$ | 1.57 g |
| $K_2HPO_4$ | 14.1 g |
| $MgSO_4 \cdot 7H_2O$ | 0.28 g |
| $H_3PO_4$ (Conc.) | 3 mL |
| Antifoam | 1 mL |
| Biotin | 0.0012 g |
| Yeast Extract | 4.6 g |
| Glycerol | 18.5 g |
| Filter sterilized ingredients | |
| $CaCl_2 \cdot 2H_2O$ (10% w/v) | 1 mL |
| Trace D Solution* | 16 mL |
| Thiamine HCl (10% w/v) | 0.1 mL |

| -continued | |
|---|---|
| Nicotinic Acid (1% w/v) | 2 mL |

*Trace D solution is composed of:

| | |
|---|---|
| $FeCl_3 \cdot 6H_2O$ | 6.480 g |
| $ZnSO_4 \cdot 7H_2O$ | 1.680 g |
| $MnCl_2 \cdot 4H_2O$ | 1.200 g |
| $Na_2MoO_4 \cdot 2H_2O$ | 0.576 g |
| $CuSO_4 \cdot 5H_2O$ | 0.240 g |
| $CoCl_2 \cdot 6H_2O$ | 0.240 g |
| $H_3BO_3$ | 0.720 g |
| $H_3PO_4$ (Conc.) | 96.0 mL |
| $H_2O$ (Batch Volume) | 2.0 L |

The fermentor was then inoculated with the bacterial seed culture, and was maintained at pH 6.0 and 32° C. with 10 L/min. air and agitation at 1000 rpm. When nutrients became limiting (as judged by an increase in the dissolved oxygen, DO, to approximately 100%), the culture was fed with additional nutrients until the culture reached an optical density ($OD_{600}$) of approximately 100. Culture feed rate was controlled to maintain the DO to a setpoint of 20%. Specifically, the culture was fed with the first feed:

| Autoclaved ingredients per liter of feed: | |
|---|---|
| Glycerol | 700 g |
| $MgSO_4 \cdot 7H_2O$ | 10 g |
| Biotin | 0.01 g |
| Filtered ingredients per liter of feed | |
| $CaCl_2 \cdot 2H_2O$ (10% w/v) | 35 mL |
| Thiamine HCl (10% w/v) | 3.5 mL |
| Nicotinic Acid (1% w/v) | 7 mL |

The culture was induced by gradient induction at an OD of approximately 100 with a second feed containing the inducing agent L-arabinose. Specifically, the second feed was:

| Autoclaved ingredients per liter of feed: | |
|---|---|
| Glycerol | 700 g |
| $MgSO_4 \cdot 7H_2O$ | 10 g |
| Biotin | 0.01 g |
| Arabinose | 60 g/L |
| Filtered ingredients per liter of feed | |
| $CaCl_2 \cdot 2H_2O$ (10% w/v) | 35 mL |
| Thiamine HCl (10% w/v) | 3.5 mL |
| Nicotinic Acid (1% w/v) | 7 mL |

The cultures were harvested 23-26 hours post induction.

The cells may be separated from the culture medium with a 0.2 µm hollow fiber cartridge, 10 $ft.^2$ (Microgon, Laguna Hills, Calif.) as described in Examples 3 and 5 below. Alternatively, the fermentation broth (i.e., culture medium with cells) may be used directly in the fermentation vessel or removed from the fermentor for acidification and further processing as described in Examples 4 and 5 below. Example 6 below describes the recovery and purification of recombinant peptides.

EXAMPLE 3

Acid Hydrolysis of Bacterial Cells and Release of Recombinant Peptide

1. Peptide Release from Bacterial Cells

Previously, inclusion bodies were isolated. Acid treatment of the isolated inclusion bodies resulted in the hydrolysis of the aspartyl-prolyl bond (Asp-Pro) between the Bone D protein and a recombinant peptide by incubation in dilute acid at elevated temperatures (see, e.g. Example 3 of U.S. Pat. No. 5,851,802). In these experiments, bacterial cells were directly acidified in an attempt to lyse the cells and hydrolyze the inclusion bodies directly to release the peptide. This was done by diluting cells in dilute acid at elevated temperature. E. coli E104 containing plasmid pING4702 was grown in a 10 L fermentor and induced with arabinose. After termination of the fermentor run, bacterial cells were separated from the majority of the culture supernatant with a 0.2 μm hollow fiber cartridge (Microgon, 10 ft$^2$) and frozen. Cells obtained from the fermentor were thawed and incubated under acidic conditions for 4 hours at 85° C. as follows in Table 1.

TABLE 1

| Sample | Cell Paste | Incubation Condition |
|---|---|---|
| A | 1 gram | 10 mL of 30 mM HCl |
| B | 1 gram | 10 mL of 30 mM HCl, 5 mM EDTA |
| C | 1 gram | 10 mL of 30 mM HCl, 5 mM EDTA, 1% Triton X-100 |
| D | 1 gram | 10 mL of 30 mM HCl, 5 mM EDTA, 8 M urea |

As a control, approximately 1 gram of cells were lysed with lysozyme and inclusion bodies were isolated prior to acid hydrolysis according to prior methods (see, e.g., Example 3 of U.S. Pat. No. 5,851,802). These cells were suspended in 10 mL of 100 mM Tris, 5 mM-EDTA, pH 8.0. The slurry was incubated on ice for 15 minutes, and 1 mL of 10 mg/ML lysozyme was added and incubated on ice for 20 minutes. To disrupt the lysozyme treated cells, the slurry was sonicated 4 times for 10 seconds each at the highest setting using a Sonic U sonicator (B. Braun Biotech Inc., Allentown, Pa.). The lysed cells were centrifuged at 13,000 rpm in a JA20 rotor for 25 minutes. The inclusion body pellet was then incubated in 10 mL of 30 mM HCl for 4 hours at 85° C.

Prior to incubation at 85° C., the pH of all samples was adjusted to pH 2.5 with HCl, except for the sample containing urea which was adjusted to pH 3.0. After incubation, the samples were centrifuged at 13,000 rpm in a JA20 rotor for 25 minutes to separate soluble from insoluble material. The amount of released peptide in the supernatant from each sample was evaluated by HPLC using a Beckman Coulter (Fullerton, Calif.) instrument with a Shimadzu Scientific Instruments (Columbia, Md.) auto injector and a Vydac (Hesperia, Calif.) C 18 (#218TP54) column. Solvent A was 10% acetonitrile/0.1% TFA; solvent B was 90% acetonitrile/0.1% TFA. The column was run with an 20-40% B gradient over 20 minutes at a flow rate of 1 mL/minute with peptide detection at 229 nm.

The concentration of peptide in the supernatant was as follows in Table 2.

TABLE 2

| | Sample | Concentration (mg/mL) | % of Control |
|---|---|---|---|
| | Purified Inclusion bodies (Control) | 0.292 | 100 |
| A | 10 mL of 30 mM HCl | 0.223 | 76.4 |
| B | 10 mL of 30 mM HCl, 5 mM EDTA | 0.218 | 74.7 |
| C | 10 mL of 30 mM HCl, 5 mM EDTA, 1% Triton X-100 | 0.287 | 98.3 |
| D | 10 mL of 30 mM HCl, 5 mM EDTA, 8 M urea | 0 | 0 |

These data demonstrate for the first time that peptide could be released directly from cells by incubation of the bacterial cells in dilute acid while the majority of other proteins remain insoluble.

2. Timecourse of Peptide Release from Bacterial Cells.

The results described above demonstrated that peptide was released from a Bone D-peptide fusion protein containing an acid sensitive Asp-Pro peptide linker by direct hydrolysis of cells in dilute acid. Studies were performed to examine the timecourse for hydrolysis. A sample of the same concentrated, frozen cell sample described above was used for additional studies. Approximately 2 grams of cell paste was diluted with 20 mL of water and concentrated HCl was added to bring the pH to 2.5. The sample was incubated at 85° C., and samples were removed periodically for quantitation. Each sample was centrifuged to remove insoluble material, and the supernatant was assayed for released peptide by HPLC. The concentration of peptide in the soluble fraction was as follows in Table 3.

TABLE 3

| Time (Hours) | Concentration by HPLC (mg/mL) |
|---|---|
| 0 | 0 |
| 0.5 | 0.02 |
| 1 | 0.03 |
| 2 | 0.056 |
| 3 | 0.082 |
| 4 | 0.142 |
| 5 | 0.184 |
| 6 | 0.219 |
| 7 | 0.267 |

Thus, as shown in Table 3, the amount of peptide in the soluble fraction was still increasing at the end of the seven hour timecourse.

In additional studies, a cell sample of bacterial cells in cell culture media was incubated at pH 2.15 to evaluate the timecourse of peptide release from cells that had not been previously concentrated and frozen. Specifically, 40 mL of bacterial cells in fermentation broth (fermentation culture of E. Coli E104 containing pING4702) at the end of the fermentor process as described in Example 2 was directly adjusted to pH 2.15 by adding 500 μL of concentrated HCl, to a final concentration of approximately 150 mM. The sample was incubated at 85° C. and every hour a sample was removed, centrifuged, and the supernatant was evaluated for peptide by HPLC. The amount of peptide released over time was as follows in Table 4.

TABLE 4

| Time (Hours) | Concentration by HPLC (mg/mL) |
|---|---|
| 0 | 0 |
| 1 | 0.062 |
| 2 | 0.218 |
| 3 | 0.321 |
| 4 | 0.350 |
| 5 | 0.366 |
| 6 | 0.392 |
| 7 | 0.432 |
| 8 | 0.401 |
| 23 | 0.298 |

At pH 2.15 and using cells directly in the fermentation medium, maximum release of peptide occurred by seven hours at 85° C., after which the amount of released peptide decreased.

Additional studies demonstrated that dilute $H_2SO_4$ and $HNO_3$ could also release soluble peptide from bacterial cells and bacterial cells in cell culture media (i.e., fermentation cultures). In studies with $H_2SO_4$, two 20 mL samples of bacterial cells in fermentation broth as described in Example 4 (fermentation culture of E. coli E104 containing pING4702) were collected after completion of a-bacterial fermentation, and they were acidified to pH 2.4. One sample was adjusted to pH 2.4 with HCl and the other was adjusted to pH 2.4 with $H_2SO_4$. Each sample was incubated at 85° C., a sample was removed every hour for seven hours and the amount of soluble peptide in each sample was analyzed by HPLC. The concentration of peptide in each aliquot is shown in the following Table 5.

TABLE 5

| | Peptide Concentration by HPLC (mg/mL) | |
|---|---|---|
| Sample Time (Hour) | HCl Hydrolysis | $H_2SO_4$ Hydrolysis |
| 0 | 0 | 0 |
| 1 | 0.034 | 0.036 |
| 2 | 0.130 | 0.116 |
| 3 | 0.185 | 0.162 |
| 4 | 0.231 | 0.209 |
| 5 | 0.281 | 0.248 |
| 6 | 0.295 | 0.275 |
| 7 | 0.303 | 0.273 |

In studies with $HNO_3$, a sample of cells in bacterial fermentation broth as described in Example 4 was incubated with nitric acid. Specifically, 20 mL of cells were adjusted to pH 2.2 with nitric acid and incubated at 85° C. Samples were removed periodically and the concentration of recombinant peptide in the soluble fraction was determined by HPLC. The concentration of peptide in each aliquot is shown in the following Table 6.

TABLE 6

| Sample Time (Hour) | Peptide Concentration by HPLC (mg/mL) after Hydrolysis with $HNO_3$ |
|---|---|
| 0 | 0 |
| 1 | 0.093 |
| 2 | 0.146 |
| 4.5 | 0.308 |
| 6 | 0.325 |

These additional studies demonstrate that acids such as nitric acid, that are less corrosive to stainless steel materials used in fermentation vessels, are useful in the improved methods of the invention.

EXAMPLE 4

Acid Hydrolysis of Bacteria Directly in a Fermentation Vessel

Since peptide was released from bacterial cells and cell cultures by direct incubation of cells in acid as described in Example 3, studies were done to evaluate if soluble peptide could be recovered directly from a bioreactor at the end of the fermentation process when contents of the fermentor were acidified and heated in place. In initial studies, E. coli E104 containing pING4702 was grown in a 35 L fermentor as described in Example 2. The first feed solution was introduced in the fermentor at 20.5 hours after inoculation, and the culture was induced with the second feed when the OD600 had reached 97.2. At 62.5 hours after induction, 10% HCl was added to the fermentor in 50 mL aliquots until the pH of the fermentor had reached approximately 2.28. In total, 990 mL of acid was added to the approximately 26 L of fermentation product in the fermentor. After reducing the pH, the temperature setpoint on the fermentor was increased to 85° C., and samples were removed from the fermentor periodically thereafter for six hours. The contents of the vessel were mixed during the reaction with the fermentor impellers. HPLC analysis of the soluble material in the samples revealed that the concentration of the peptide leveled off between four and five hours. The concentration of peptide was as shown in the following Table 7.

TABLE 7

| Sample Timepoint (Hours) | Peptide Concentration by HPLC (mg/mL) |
|---|---|
| 0 | 0 |
| 1 | 0.185 |
| 2 | 0.294 |
| 3 | 0.334 |
| 4 | 0.353 |
| 5 | 0.353 |
| 6 | 0.370 |

In additional studies, E. coli E104 containing pING4702 was grown in a 35 L fermentor to an OD600 of 89, induced with the second feed containing arabinose and grown for 24 hours. A 10% HCl solution was added to bring the culture pH to approximately 2.3, and the temperature was raised to 85° C. for 5.5 hours. The concentration of peptide in the soluble fraction was 0.332 mg/mL.

EXAMPLE 5

Acid Hydrolysis of Bacteria After Removal of the Cell Culture Medium

E. coli E104 containing pING4703 was grown in a 14 L fermentor as described in Example 2, and 10 mL of the fermentation culture was adjusted to pH 2.2 with concentrated HCl. The sample was incubated at 85° C., and samples were taken every few hours and analyzed for peptide in the supernatant by HPLC, using the same method as described in Example 3 for quantitation of peptide from the product encoded by pING4702. The results from this study are shown in the following Table 8.

TABLE 8

| Time at 85° C. | Peptide Concentration mg/mL |
|---|---|
| 4 | 0.018 |
| 6 | 0.011 |
| 7 | 0.004 |

These peptide titers were much lower than what was obtained with cultures of *E. coli* E104 (pING4702) as described in Examples 3 and 4, and lower than the titer obtained when *E. coli* E104 (pING4703) was lysed by sonication after incubation with lysozyme by the process described in Example 3. *E. coli* E104 (pING4703) lysed by sonication after lysozyme treatment had a titer of approximately 0.46 mg/mL in the soluble fraction.

In additional studies, samples of the bacterial cell culture both before and after acid hydrolysis at 85° C. were analyzed by SDS-PAGE. The results demonstrated that the fusion protein of Bone D and peptide had been hydrolyzed by acid. An experiment was executed to determine if the cell culture medium in the hydrolysis reaction had an impact on the ability to recover recombinant peptide in the soluble fraction, since a prominent band at the position of Bone D was apparent in the hydrolyzed sample, while very little intact fusion protein was detected. Cell paste from the fermentation of *E. coli* E104 (pING4703) was prepared by centrifugation, and 1 g of cell paste was suspended in: 7 mL H2O; 7 mL of 5 mM EDTA; or 7 mL of cell-free fermentation broth from the same bacterial fermentor. Each sample was adjusted to pH 2.2 with concentrated HCl, and incubated at 85° C. The amount of recombinant peptide in the soluble fraction was measured over time by HPLC. The results are shown in the following Table 9.

TABLE 9

| Time (Hours) at 85° C. | H₂O Sample | 5 mM EDTA Sample | Medium Sample |
|---|---|---|---|
| | Peptide Concentration by HPLC (mg/mL) | | |
| 1 | 0.052 | 0.043 | 0 |
| 2 | 0.184 | 0.187 | 0.011 |
| 4 | 0.269 | 0.284 | 0.009 |
| 6 | 0.267 | not determined | 0.003 |
| 8 | 0.255 | not determined | not determined |

These data demonstrated that the recombinant peptide was soluble when the cells were hydrolyzed in water or 5 mM EDTA, but did not become soluble in the fermentation medium after acid hydrolysis.

Further studies were performed to determine if recombinant peptide was insoluble in acid after hydrolysis from Bone D, and could be released from the insoluble material in detergents or chaotropic salts. Three 1 gram samples of cell paste from *E. coli* E104 (pING4703) were suspended in 7 mL of 100 mM Tris, 5 mM EDTA, pH 8.0, and one 1 gram sample of cell paste was suspended in 7 mL of cell-free culture medium from the *E. coli* fermentation. To one of the samples suspended in Tris buffer, 1 mL of 10 mg/mL lysozyme was added, the sample was incubated on ice and sonicated as described in Example 3. The pH of all four samples was adjusted to approximately pH 2.0 with concentrated HCl, and the samples were incubated at 85° C. for 4 hours. By HPLC, the amount of peptide released into the soluble fraction from the four samples was as follows in Table 10.

TABLE 10

| Sample | Suspension buffer | Peptide Concentration mg/mL |
|---|---|---|
| 1 | 100 mM Tris, 5 mM EDTA | 0.594 |
| 2 | 100 mM Tris, 5 mM EDTA | 0.618 |
| 3 | Medium | 0 |
| 4 | 100 mM Tris, 5 mM EDTA + Lysozyme and sonication | 0.519 |

Thus, peptide did not appear in the soluble fraction in Sample 3 after acid hydrolysis. To determine if peptide could be released from the insoluble material, the pellet from Sample 3 was washed sequentially with 7 mL of buffer containing Triton X-100, urea, guanidine hydrochloride or SDS. The amount of peptide released from the pellet was as follows in Table 11.

TABLE 11

| Wash Buffer | Peptide concentration (mg/mL) in the Wash Buffer | Total Peptide Released mg peptide/gram of cells |
|---|---|---|
| 1% Triton X-100 in 10 mM sodium phosphate, pH 7.0 | 0.01 | 0.08 |
| 3% Triton S-100 in 10 mM sodium citrate, pH 3.0 | 0 | 0 |
| 4 M urea in 10 mM sodium citrate, pH 3.0 | 0.04 | 0.29 |
| 8 M urea in 10 mM sodium citrate, pH 3.0 - first wash | 0.08 | 0.55 |
| 8 M urea in 10 mM sodium citrate, pH 3.0 - second wash | 0.07 | 0.49 |
| 8 M urea in 10 mM sodium citrate, pH 3.0-third wash for 15 hours | 0.06 | 0.39 |
| 6 M guanidine hydrochloride | 0.12 | 0.87 |
| 4% SDS | 0 | 0 |
| Total in all washes: | | 2.67 |

These results demonstrated that the peptide could be recovered from the insoluble material by washing in buffers containing urea or guanidine hydrochloride. The peptide was therefore not degraded by the hydrolysis condition, but is rendered insoluble by media components. The total amount of material recoverable in all washes was 2.67 mg per gram of cells, compared to 4.16 mg/g and 3.63 mg/g recovered directly from the soluble material in Samples 1 and 4 respectively. Thus, for some bacterial cell cultures, the bacterial cells may be preferentially removed from the media and the bacterial cells may be acidified according to Example 3. For other bacterial cell cultures, the fermentation broth (bacterial cells in cell culture/fermentation media) may be directly acidified according to Examples 3 and 4.

EXAMPLE 6

Recovery and Purification of Recombinant Peptide from Acid Hydrolyzed Cells

1. Recovery

The invention provides methods for the recovery of peptides in the soluble fraction after acid hydrolysis of cells while the large majority of other bacterial proteins, the carrier protein, and other impurities remain in the insoluble fraction. The soluble and insoluble material can be separated by centrifugation, filtration or any other suitable separation method. Any variety of centrifuge can be used to separate these materials and a variety of filtration devices, systems and methods can also be used. A variety of such filtration devices, systems and methods were used to separate soluble and insoluble materials including dead end (depth) filtration and tangential flow filtration. A summary of the results of exemplary filtration studies to separate soluble and insoluble material by filtration is presented in the following Table 12.

TABLE 12

| Filtration Method | Sample Analyzed | Filter Description | Throughput | Permeate description | Recovery |
|---|---|---|---|---|---|
| Depth | Previously frozen cell paste suspended in water and acid hydrolyzed | Seitz 900 SD/SDC, 1 ft², 8 µm nominal retention | 1.5 L | Clear | 72% |
| Depth preceded by 1 µm bag filter | Previously frozen cell paste suspended in 4 volumes of water and acid hydrolyzed | Seitz SD250, 1 ft², 4 µm nominal retention | 5.5 L | Clear | 94% |
| Depth | Acid hydrolysate prepared directly in a 35 L fermentor | Cuno Zeta Plus 01A, 1 ft², 7 µm nominal retention | 1.7 L | Cloudy | ND |
| Depth preceded by 1 µm bag filter | Acid hydrolysate prepared directly in a 35 L fermentor | Cuno 30 SP, 1 ft², 0.6 µm nominal retention | 1.2 L | Cloudy | ND |
| Depth with and without Celite filter aid | Previously frozen cell paste suspended in 3.8 volumes of water and acid hydrolyzed | Cuno Zeta Plus 01A, 28 cm² | 27 mL with no Celite; >50 mL with Celite (HP³ 1000) | Slightly cloudy | ND |
| Celite filter aid in horizontal pressure leaf vessel | Acid hydrolysate prepared directly in a 35 L fermentor | Celite (Hy-flo) precoat, 600 cm² | 2 L/min | Clear | 73% |
| Tangential Flow | Previously frozen cell paste suspended in 3.8 volumes of water and acid hydrolyzed | Sartorius 0.2 cutoff filter, 0.1 m² | ND | Cloudy | ND |
| Tangential Flow | Previously frozen cell paste suspended in 3.8 volumes of water and acid hydrolyzed | 300 kDa MWCO, 0.1 m² | 150 mL/min | Clear | 81% |

ND—not determined
Seitz filters are products of SWK Filtration Incorporated, Petaluma, CA.
Cuno filters are products of Cuno, Meriden, CT.
Celite is a product of World Minerals, Lompoc, CA.
Sartorius filters are products of Sartorius, Edgewood, NY.

These results demonstrate that a variety of filtration devices, systems and methods can be successfully employed to separate the soluble and insoluble material.

2. Purification

Following fermentation of *E. coli* E104 containing pING4702 as described in Example 2, bacterial cells in the unprocessed fermentation broth were hydrolyzed in dilute HCl. Specifically, 40 mL of fermentation broth was adjusted to pH 2.15 with concentrated HCl. The sample was incubated at 85° C. for 5.5 hours. The hydrolyzed cells were then centrifuged to remove insoluble material, and the supernatant was adjusted to pH 3.0 by adding 500 mM sodium citrate dropwise.

An SP Sepharose (Amersham-Pharmacia, Piscataway, N.J.) column, 2.5×4.4 cm containing 21.6 mL, was equilibrated in 10 mM sodium citrate, pH 3.0 and the sample was loaded. The column was washed with 10 mM sodium citrate, pH 3.0 buffer and then 10 mM sodium phosphate, pH 7.0 until the pH of the column effluent reached 7. The column was then washed in 10 mM sodium phosphate, 150 mM NaCl pH 7.0. The column was eluted in 10 mM sodium phosphate, 800 mM NaCl pH 7.0 and then the column was stripped with 10 mM sodium phosphate, 2 M NaCl. The SP Sepharose eluate was diluted with one volume of 10 mM sodium phosphate, 3 M ammonium sulfate, pH 7.0.

A Butyl Sepharose (Amersham-Pharmacia) column, 1×4 cm containing 3.1 mL, was equilibrated with 10 mM sodium phosphate, 1.5 M ammonium sulfate, pH 7.0, and the sample was loaded. The Butyl Sepharose column was washed with 10 mM sodium phosphate, 1.1 M ammonium sulfate, pH 7.0, and then eluted with 10 mM sodium phosphate, 0.4 M ammonium sulfate, pH 7.0. The column was striped with 10 mM sodium phosphate, pH 7.0

The peptide concentration in each of the fractions from the SP Sepharose and Butyl Sepharose columns was followed by HPLC analysis. The sample volumes, peptide concentrations and percent recovery was as follows in Table 13.

TABLE 13

| Sample | Volume (mL) | Concentration (mg/mL) | Total mg | % Yield |
|---|---|---|---|---|
| SP Sepharose load | 24 | 0.399 | 9.58 | 100 |
| First SP Sepharose wash | 75 | 0 | 0 | 0 |
| Second SP Sepharose wash | 33 | 0 | 0 | 0 |
| SP Sepharose eluate | 50 | 0.165 | 8.25 | 86.1 |
| SP Sepharose strip | 13 | 0.036 | 0.47 | 4.9 |
| Butyl Sepharose load | 94 | ND | ND | ND |
| Butyl Sepharose flow through | 95 | 0 | 0 | 0 |
| Butyl Sepharose wash | 13 | 0.008 | 0.1 | 1 |
| Butyl Sepharose eluate | 28 | 0.262 | 7.34 | 76.6 |
| Butyl Sepharose strip | 4 | 0.014 | 0.06 | 0.6 |

ND—Not Determined

A Superdex 30 (Amersham-Pharmacia) column, 1.6×53 cm containing 107 mL, was equilibrated in 5 mM sodium acetate, 150 mM NaCl, pH 5.0. Eight mL of Butyl Sepharose eluate was loaded onto the Superdex 30 gel filtration column, and the column was run with 5 mM sodium acetate, 150 mM NaCl, pH 5.0. After 32 mL had flowed through the column, 3 mL fractions were collected. Fractions 12-19 were pooled and had a volume of approximately 20 mL. The concentration of recombinant peptide in the Superdex 30 pool was 0.107 mg/mL for a recovery of 102% from the previous step, and the overall recovery from the acid hydrolysate of cells was 76.6%. The final peptide purity was 97.4%.

EXAMPLE 7

Biological Activity Assays of Recombinant Peptides

A variety of recombinant peptides, including those BPI-derived peptides comprising the sequences listed in U.S. Pat. No. 5,851,802 incorporated by reference, may be produced by recombinant methods of the invention and tested for biological activity by known activity assays. Assays for antimicrobial activity (both anti-fungal and anti-bacterial activity) may be performed, including radial diffusion assays. Assays, with a variety of fungal and bacterial cells, including those described in U.S. Pat. No. 5,851,802 (see Example 6), may be conducted using recombinant peptides produced according to the invention.

For example, studies were performed to evaluate the antifungal activity of the recombinant peptide from pING4702 purified according to Example 6 in a broth microdilution assay using four strains of C. albicans, C. glabrata and S. cerevisiae. A similar peptide, XMP.391, that was chemically synthesized, was included in the assay as a positive control. To perform the broth microdilution assay, the fungal cultures were grown overnight at 30° C. in YPD medium (1% yeast extract, 2% peptone, and 2% dextrose). A 400 fold dilution of each culture in YPD was then made, and grown at 30° C. for 8 hours. Three mL of each culture were collected by centrifugation and suspended in 0.9% NaCl to an A600 of about 0.3. These cultures were further diluted to $1 \times 10^4$ CFU/mL in Sabouraud dextrose broth (6 mL). Recombinant peptide was in 5 mM acetate, 150 mM NaCl, pH 5.0 at a concentration of about 2 mg/mL. Synthetic peptide was at about 1 mg/mL. Samples were serially diluted and added to microtiter plates containing the cultures. Plates were incubated at 30° C. for 48 hours before growth inhibition was measured. Results from this assay were as follows in Table 14.

TABLE 14

| Strain | Synthetic Peptide XMP.391 (Concentration that gives 95% inhibition (μM)) | Recombinant Peptide (Concentration that gives 95% inhibition (μM)) |
| --- | --- | --- |
| C. albicans SLU1 | 13.5 | 16 |
| C. albicans 10231 | 16 | 30 |
| C. albicans 14053 | 16 | 16 |
| C. albicans 26555 | 16 | 30 |
| C. glabrata 2001 | 30 | 30 |
| S. cerevisiae 9763 | 2.0 | 7.5 |

Additionally or alternatively, assays may be performed to assess the endotoxin binding and neutralizing activity of the recombinantly produced peptides, by a variety of known assays, including those described in co-owned U.S. Pat. Nos. 5,733,872 and 5,763,567 [WO 94/20532 (PCT/US94/02465)]; 5,652,332 and 5,856,438 [WO 95/19372 (PCT/US94/10427)]; 5,858,974 [WO 96/08509 (PCT/US95/09262) and WO 97/04008 (PCT/US96/03845)]; incorporated by reference in their entirety.

Additionally or alternatively, assays may be performed to assess the heparin binding and neutralizing activity of the recombinantly produced peptides by a variety of known assays, including assays as described in U.S. Pat. Nos. 5,348,942; 5,639,727; 5,807,818; 5,837,678; and 5,854,214 [WO 94/20128 (PCT/US94/02401)]; 5,733,872 and 5,763,567 [WO 94/20532 (PCT/US94/02465)]; 5,652,332 and 5,856,438 [WO 95/19372 (PCT/US94/10427)]; incorporated by reference in their entirety.

It should be understood that the foregoing disclosure emphasizes certain specific embodiments of the invention and all modifications or alternatives equivalent thereto are within the spirit and scope of the invention as set forth in the appended claims. In particular, numerous modifications and variations in the practice of the invention are expected to occur to those skilled in the art upon consideration of the foregoing description on the presently preferred embodiments thereof. Consequently, the only limitations which should be placed upon the scope of the present invention are those that appear in the appended claims.

What is claimed is:

1. A method for obtaining a peptide from bacterial cells after expression inside the cells of a fusion protein, wherein the fusion protein comprises the peptide, a carrier protein and an acid-cleavable site between the peptide and the carrier protein, the method comprising: treating the bacterial cells for one or more hours with acid under conditions of acid pH and temperature sufficient in a single step to disrupt or lyse the cells and release the peptide from the fusion protein.

2. The method of claim 1 with the additional step of obtaining the released peptide separated from the disrupted or lysed cells.

3. The method of claim 2 wherein the released peptide is separated from the disrupted or lysed cells by a separation device.

4. The method of claim 3 wherein the separation device is a centrifugation device.

5. The method of claim 3 wherein the separation device is a filtration device.

6. The method of claim 1 wherein the acid-cleavable site in the fusion protein is Asp-Pro.

7. The method of claim 1 wherein the carrier protein is expressed as an insoluble protein inside the bacterial cells.

8. The method of claim 7 wherein the carrier protein is the D subunit of human osteogenic protein.

9. The method of claim 1 wherein the bacterial cells are in cell culture media for the acid treatment.

10. The method of claim 1 wherein the bacterial cells have been separated from cell culture media for the acid treatment.

11. The method of claim 1 wherein the bacterial cells are in cell culture media in a fermentation vessel for the acid treatment.

12. A method for obtaining a peptide from bacterial cells after expression inside the cells of a fusion protein, wherein the fusion protein comprises the peptide, a carrier protein and an acid-cleavable site between the peptide and the carrier protein, the method comprising:

(a) treating the bacterial cells with acid for one or more hours under conditions of acid pH and temperature sufficient to disrupt or lyse the cells and release the peptide from the fusion protein, (b) separating soluble material from insoluble material after step (a), and (c) recovering the released peptide in the soluble material after step (b).

13. The method of claim 12 wherein the soluble material is separated from the insoluble material by a separation device.

14. The method of claim 13 wherein the separation device is a centrifugation device.

15. The method of claim 13 wherein the separation device is a filtration device.

16. The method of claim 12 wherein the acid-cleavable site in the fusion protein is Asp-Pro.

17. The method of claim 12 wherein the carrier protein is expressed as an insoluble protein inside the bacterial cells.

18. The method of claim 17 wherein the carrier protein is the D subunit of human osteogenic protein.

19. The method of claim 12 wherein the bacterial cells are in cell culture media for the acid treatment.

20. The method of claim 12 wherein the bacterial cells have been separated from cell culture media for the acid treatment.

21. The method of claim 12 wherein the bacterial cells are in cell culture media in a fermentation vessel for the acid treatment.

* * * * *